United States Patent
Gu

(10) Patent No.: US 10,842,452 B2
(45) Date of Patent: Nov. 24, 2020

(54) SYSTEMS AND METHODS FOR CONTROLLING AN X-RAY IMAGING DEVICE

(71) Applicant: SHANGHAI UNITED IMAGING HEALTHCARE CO., LTD., Shanghai (CN)

(72) Inventor: Jie Gu, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 204 days.

(21) Appl. No.: 15/964,040

(22) Filed: Apr. 26, 2018

(65) Prior Publication Data

US 2018/0242936 A1    Aug. 30, 2018

Related U.S. Application Data

(63) Continuation of application No. PCT/CN2017/120239, filed on Dec. 29, 2017.

(30) Foreign Application Priority Data

Jan. 19, 2017    (CN) .......................... 2017 1 0038617

(51) Int. Cl.
*H05G 1/02*    (2006.01)
*A61B 6/00*    (2006.01)
*A61B 6/10*    (2006.01)

(52) U.S. Cl.
CPC ............ *A61B 6/4429* (2013.01); *A61B 6/105* (2013.01); *A61B 6/4464* (2013.01);
(Continued)

(58) Field of Classification Search
CPC ........... A61B 6/00; A61B 6/102; A61B 6/105; A61B 6/42; A61B 6/4405; A61B 6/4429;
(Continued)

(56) References Cited

U.S. PATENT DOCUMENTS 4,501,011 A    2/1985 Hauck et al.
5,048,070 A    9/1991 Maehama et al.
(Continued)

FOREIGN PATENT DOCUMENTS

CN    106725557 A    5/2017

OTHER PUBLICATIONS

International Search Report for PCT/CN2017/120239 dated Mar. 29, 2013, 6 pages.
(Continued)

*Primary Examiner* — Irakli Kiknadze
(74) *Attorney, Agent, or Firm* — Metis IP LLC

(57)    ABSTRACT

A method for controlling the movement of an X-ray source via a suspension device includes obtaining, during a movement of the suspension device along the rail, a first speed of the suspension device at the first reference point. The first reference point may correspond to a first target position. The method may also include determining whether the first speed of the suspension device at the first reference point is less than a threshold speed. In response to a result of the determination that the first speed of the suspension device at the first reference point is less than the threshold speed, the method may further include actuating a control device to move the suspension device to the first target position.

20 Claims, 9 Drawing Sheets

(52) U.S. Cl.
CPC .......... *A61B 6/4476* (2013.01); *A61B 6/4482* (2013.01); *A61B 6/467* (2013.01); *A61B 6/4405* (2013.01)

(58) Field of Classification Search
CPC ....... A61B 6/4476; A61B 6/54; A61B 6/4464; A61B 6/467; A61B 6/547; A61B 6/4283; A61B 6/548; A61B 6/583; A61B 2017/00716; A61B 2017/00725; A61B 5/055; A61B 6/037; A61B 6/4233; A61B 6/032; A61B 6/0457; A61B 6/40; A61B 6/4085; A61B 6/542; A61B 6/588; A61B 6/4441; A61B 6/035; A61B 6/027; A61B 6/04; A61B 6/4417; A61B 6/4482; G06T 7/0004; H04L 1/0002; H04L 1/0041; H04L 1/18; H04L 5/0064; H04L 67/1097; H04L 67/12; H04L 1/0009; H04L 1/1874; H04L 67/306; H04L 1/187; H04L 67/04; H04L 67/10; G05B 19/4183; G05B 23/0221; G05B 13/028; G05B 19/4184; G05B 19/41845; G05B 19/4185; G05B 19/41865; G05B 19/41875; G05B 2219/32287; G05B 2219/35001; G05B 2219/37337; G05B 2219/37351
USPC ................................ 378/196, 197, 205, 207
See application file for complete search history.

(56) References Cited

U.S. PATENT DOCUMENTS

| | | | | |
|---|---|---|---|---|
| 5,159,622 | A | * | 10/1992 | Sakaniwa ................ A61B 6/00 378/196 |
| 5,185,778 | A | * | 2/1993 | Magram .............. A61B 6/4482 378/196 |
| 5,636,259 | A | * | 6/1997 | Khutoryansky ......... A61B 6/00 378/197 |
| 5,870,450 | A | * | 2/1999 | Khutoryansky ..... A61B 6/4283 378/181 |
| 6,470,519 | B1 | | 10/2002 | Pattee et al. |
| 7,090,396 | B2 | * | 8/2006 | Boomgaarden ...... A61B 6/4464 378/196 |
| 7,165,885 | B2 | * | 1/2007 | Lumma ................ A61B 6/105 378/167 |
| 2006/0126795 | A1 | | 6/2006 | Lumma |
| 2007/0078534 | A1 | | 4/2007 | Boomgaarden |
| 2007/0121791 | A1 | | 5/2007 | Haupl et al. |
| 2010/0299014 | A1 | | 11/2010 | Bouvier |
| 2013/0003939 | A1 | | 1/2013 | Bouvier et al. |
| 2016/0113605 | A1 | | 4/2016 | Bouvier et al. |

OTHER PUBLICATIONS

Written Opinion of the International Searching Authority for PCT/CN2017/120239 dated Mar. 29, 2018, 5 pages.
The Search Report in Russian Application: No. 2019122623 dated Feb. 27, 2020, 4 pages.

* cited by examiner

SYSTEMS AND METHODS FOR CONTROLLING AN X-RAY IMAGING DEVICE

CROSS-REFERENCE TO RELATED APPLICATION

This application is a continuation of International Application No. PCT/CN2017/120239, filed on Dec. 29, 2017, which claims priority to Chinese Patent Application No. 201710038617.6, filed on Jan. 19, 2017, the entire contents of the above-referenced applications are hereby incorporated by reference.

TECHNICAL FIELD

The present disclosure generally relates to X-ray imaging, and more particularly, to systems and methods for controlling the movement of an X-ray source via a suspension device.

BACKGROUND

X-ray imaging has been widely used in clinical examinations and medical diagnoses in recent years. When using an X-ray imaging device to perform a scan, a user (e.g., a doctor, a technician) needs to control the X-ray imaging device. For example, the doctor may need to move the X-ray source of the X-ray imaging device to a target position to perform a scan. Therefore, it is desirable to provide systems and methods for moving the X-ray source of the X-ray imaging device to the target position efficiently.

SUMMARY

According to an aspect of the present disclosure, a system may include an X-ray imaging device, a control device, a storage device storing a set of instructions, and at least one processor configured to communicate with the storage device. The X-ray imaging device may include a suspension device. The suspension device may include an X-ray source and be suspended from a rail. The suspension device may be movable along the rail. The rail may include a first target position and a first reference point corresponding to the first target position. The control device may be configured to control the suspension device. When executing the set of instructions, the at least one processor may cause the system to obtain, during a movement of the suspension device along the rail, a first speed of the suspension device at the first reference point. The at least one processor may also cause the system to determine whether the first speed of the suspension device at the first reference point is less than a threshold speed. In response to a determination that the first speed of the suspension device at the first reference point is less than the threshold speed, the at least one processor may cause the system to actuate the control device to move the suspension device to the first target position.

In some embodiments, the suspension device may have a locked state and a manual movement state. Under the locked state, the suspension device may be configured to be locked onto the rail. Under the manual movement state, the suspension device may be configured to be manually moved by a user. The suspension device may operate in the locked state at an initial position of the suspension device on the rail. The at least one processor may also cause the system to obtain a request to unlock the suspension device, and actuate the control device to switch the suspension device from the locked state to the manual movement state.

In some embodiments, the suspension device may further have an automatic movement state. Under the automatic movement state, the suspension device may be configured to be moved by the control device. The at least one processor may also cause the system to actuate the control device to switch the suspension device from the manual movement state to the automatic movement state.

In some embodiments, the at least one processor may also cause the system to actuate the control device to switch the suspension device from the automatic movement state to the locked state at the first target position.

In some embodiments, the control device may include a clutch and a motor. The suspension device may operate in the locked state when the clutch is closed and the motor is turned off. The suspension device may operate in the manual movement state when the clutch is open and the motor is turned off. The suspension device may operate in the automatic movement state when the clutch is closed and the motor is turned on.

In some embodiments, the rail may further include a second target position and a second reference point corresponding to the second target position. In response to a determination that the first speed of the suspension device at the first reference point is not less than the threshold speed, the at least one processor may cause the system to maintain the suspension device in the manual movement state. The at least one processor may also cause the system to obtain, during a movement of the suspension device along the rail, a second speed of the suspension device at the second reference point. The at least one processor may further cause the system to determine whether the second speed of the suspension device at the second reference point is less than the threshold speed. In response to the determination that the second speed of the suspension device at the second reference point is less than the threshold speed, the at least one processor may cause the system to actuate the control device to move the suspension device to the second target position.

In some embodiments, the rail may include a plurality of first reference points corresponding to the first target position. At least one of the plurality of first reference points may locate on one side of the first target position and at least one of the plurality of first reference points may locate on another side of the first target position along the rail.

In some embodiments, the at least one processor may also cause the system to determine the first reference point corresponding to the first target position on the rail. A distance between the first reference point and the first target position may be less than a predetermined distance.

In some embodiments, the predetermined distance may be less than 90 mm, 100 mm, or 110 mm.

In some embodiments, the first target position may be associated with a source to image receptor distance (SID) of the X-ray imaging device.

According to another aspect of the present disclosure, a computer-implemented method may include one or more of the following operations performed by at least one processor. The method may include obtaining, during a movement of a suspension device along a rail, a first speed of the suspension device at a first reference point on the rail. The suspension device may include an X-ray source and be suspended from the rail. The suspension device may be movable along the rail. The first reference point may correspond to a first target position on the rail. The method may also include determining whether the first speed of the suspension device at the first reference point is less than a threshold speed. In response to a determination that the first speed of the suspension device at the first reference point is less than the threshold speed, the method may further include actuating a control device to move the suspension device to the first target position.

According to yet another aspect of the present disclosure, a non-transitory computer-readable storage medium storing instructions that, when executed by at least one processor of a system, cause the system to perform a method. The method may include obtaining, during a movement of a suspension device along a rail, a first speed of the suspension device at a first reference point on the rail. The suspension device may include an X-ray source and be suspended from the rail. The suspension device may be movable along the rail. The first reference point may correspond to a first target position on the rail. The method may also include determining whether the first speed of the suspension device at the first reference point is less than a threshold speed. In response to a determination that the first speed of the suspension device at the first reference point is less than the threshold speed, the method may further include actuating a control device to move the suspension device to the first target position.

According to yet another aspect of the present disclosure, a system may include an acquisition module, a determination module, and a control module. The acquisition module may be configured to obtain, during a movement of a suspension device along a rail, a first speed of the suspension device at a first reference point on the rail. The suspension device may include an X-ray source and be suspended from the rail. The suspension device may be movable along the rail. The first reference point may correspond to a first target position on the rail. The determination module may be configured to determine whether the first speed of the suspension device at the first reference point is less than a threshold speed. The control module may be configured to actuate a control device to move the suspension device to the first target position in response to a determination that the first speed of the suspension device at the first reference point is less than the threshold speed.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

Figure 1:
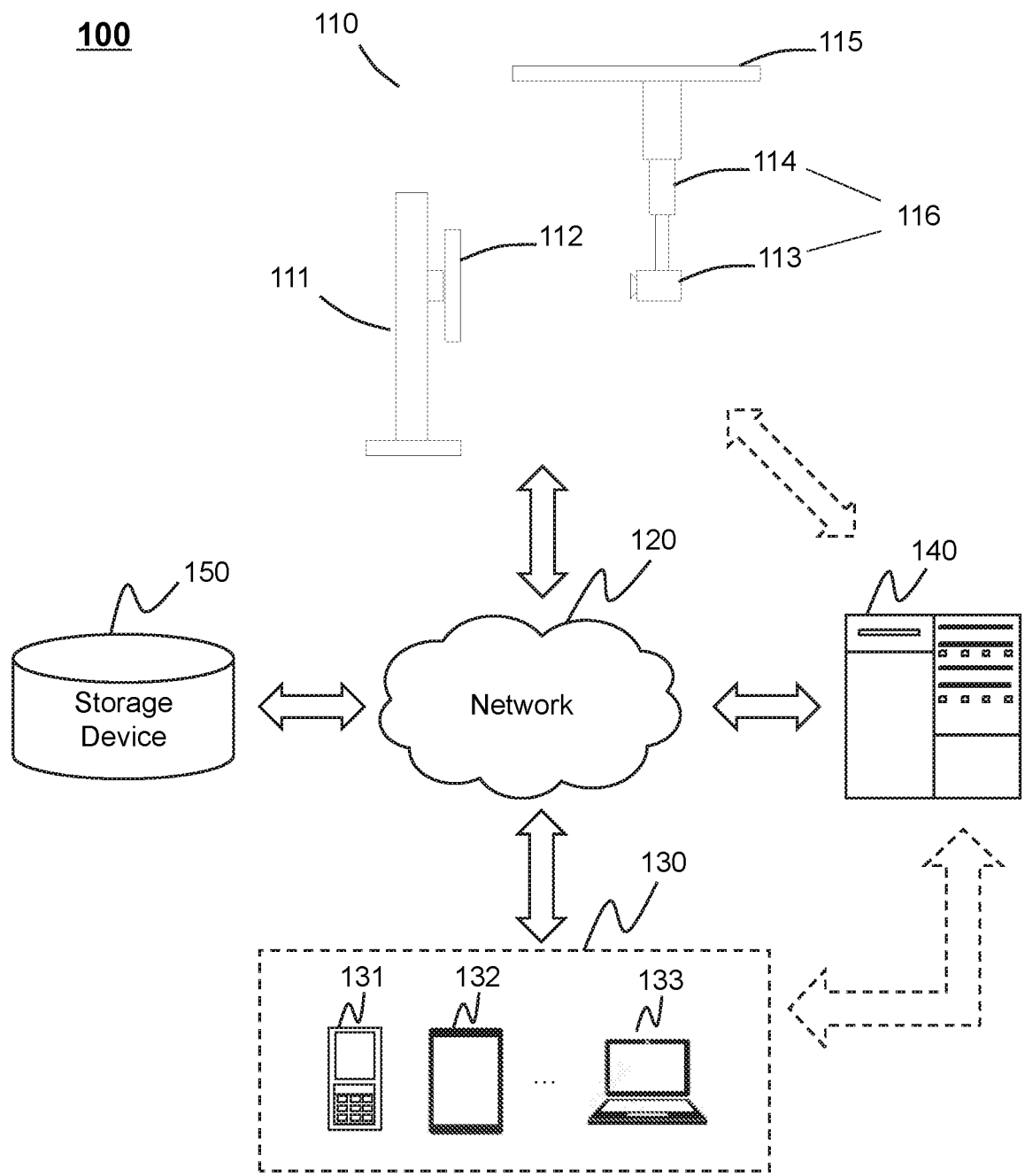
FIG. 1 is a schematic diagram illustrating an exemplary X-ray imaging system according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is to describe particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, section or assembly of different level in ascending order. However, the terms may be displaced by another expression if they achieve the same purpose.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or themselves, and/or may be invoked in response to detected events or interrupts. Software modules/units/blocks configured for execution on computing devices (e.g., the processor 210 illustrated in FIG. 2 and/or the CPU 340 illustrated in FIG. 3) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may apply to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

Provided herein are systems and components for medical imaging. In some embodiments, the imaging system may include a single modality imaging system and/or a multi-modality imaging system. The single modality imaging system may include, for example, an X-ray imaging system. The multi-modality imaging system may include, for example, an X-ray imaging-magnetic resonance imaging (X-ray-MRI) system, a positron emission tomography-X-ray imaging (PET-X-ray) system, etc. For illustration purposes, the disclosure describes systems and methods relating to X-ray imaging system. It should be noted that the X-ray imaging system described below is merely provided for illustration purposes, and not intended to limit the scope of the present disclosure.

An aspect of the present disclosure relates to systems and methods for controlling an X-ray imaging device. The X-ray imaging device may include a suspension device. The suspension device may include an X-ray source and be suspended from a rail. The suspension device may be movable and configured to move along the rail. The rail may include a target position for the suspension device and a reference point corresponding to the target position. The systems may perform the methods to obtain a speed of the suspension device at the reference point during a movement of the suspension device along the rail. The systems may perform the methods to determine whether the speed of the suspension device at the reference point is less than a threshold speed. Upon the determination that the speed of the suspension device at the reference point is less than the threshold speed, the systems may perform the methods to actuate a control device to move the suspension device to the target position.

FIG. 1 is a schematic diagram illustrating an exemplary X-ray imaging system 100 according to some embodiments of the present disclosure. As shown in FIG. 1, the X-ray imaging system 100 may include an X-ray imaging device 110, a network 120, one or more terminals 130, a processing engine 140, and a storage device 150. The connection between the components in the X-ray imaging system 100 may be variable. For example, the X-ray imaging device 110 and/or the terminal(s) 130 may be connected to the processing engine 140 through the network 120. As another example, the X-ray imaging device 110 and/or the terminal(s) 130 may be connected to the processing engine 140 directly.

The X-ray imaging device 110 may be configured to scan an object using X-rays and generate imaging data used to generate one or more images relating to the object. In some embodiments, the X-ray imaging device 110 may transmit the imaging data to the processing engine 140 for further processing (e.g., generating one or more images). In some embodiments, the imaging data and/or the one or more images associated with the object may be stored in the storage device 150 and/or the processing engine 140.

In some embodiments, the X-ray imaging device 110 may be a suspended X-ray imaging device. The object may be biological or non-biological. Merely by way of example, the object may include a patient, a man-made object, etc. As another example, the object may include a specific portion, organ, and/or tissue of a patient. For example, the object may include head, brain, neck, body, shoulder, arm, thorax, cardiac, stomach, blood vessel, soft tissue, knee, feet, or the like, or any combination thereof.

In some embodiments, the X-ray imaging device 110 may be a suspended X-ray imaging device as illustrated in FIG. 1. The X-ray imaging device 110 may include a support 111, a detector 112, a rail 115, and a suspension device 116. The support 111 may be configured to support the detector 112. In some embodiments, the support 111 may have a column-shape as illustrated in FIG. 1. Alternatively, the support 111 may have any other shape, such as a C-shape, an O-shape, a U-shape, a G-shape, or the like, or a combination thereof.

The suspension device 116 may include a suspension holder 114 and an X-ray source 113. The suspension holder 114 may be configured to suspend the X-ray source 113 from the rail 115. In some embodiments, the suspension device 116 may be movable and configured to move along the rail 115, and the X-ray source 113 may move with the suspension device 116. For example, a user may move the suspension holder 114 or another part of the suspension device 116 to move the X-ray source 113 to a desired position. Alternatively or additionally, the suspension device 116 may be automatically moved along the rail by a control device. In some embodiments, the rail 115 may include one or more target positions for the suspension device 116. The suspension device 116 may be moved to a target position manually by a user or automatically by a control device so that the X-ray source 113 may scan the object at a desired position (i.e., the position of the X-ray source 113 corresponding to the target position to which the suspension device 116 is moved). In some embodiment, a control panel (not shown in FIG. 1) may be mounted on the suspension device 116. A user may control the suspension device 116 via the control panel. Details regarding the suspension device 116 may be found elsewhere in the present disclosure (e.g., FIGS. 5 to 9 and the relevant descriptions thereof).

The X-ray source 113 may emit one or more X-rays to the object. In some embodiments, the X-ray source 113 may include an X-ray tube (not shown in FIG. 1) and a beam limiting device (not shown in FIG. 1). The X-ray tube may be configured to emit one or more X-ray beams toward an object to be scanned. The beam limiting device may be configured to control the irradiation region on the object. The beam limiting device may also be configured to adjust the intensity and/or the number of the X-ray beams that irradiate on the object.

The detector 112 may detect radioactive rays emitted from the X-ray source 113. In some embodiments, the detector 112 may be configured to produce an analog electrical signal that represents the intensity of the received X-rays, including the attenuated beam, as it passes through the object. In some embodiments, the detector 112 may include one or more detector units. The detector units may include a scintillation detector (e.g., a cesium iodide detector), a gas detector, etc. The pixels of the detector may be represented by the number of the smallest detector units, e.g., the number of detector units. The detector units of the detector 112 may be arranged in a single row, two rows, or another number of rows. The X-ray detector may be one-dimensional, two-dimensional, or three-dimensional.

The network 120 may include any suitable network that can facilitate the exchange of information and/or data for the X-ray imaging system 100. In some embodiments, one or more components of the X-ray imaging system 100 (e.g., the X-ray imaging device 110, the terminal 130, the processing engine 140, the storage device 150) may communicate information and/or data with one or more other components of the X-ray imaging system 100 via the network 120. For example, the processing engine 140 may obtain image data from the X-ray imaging device 110 via the network 120. As another example, the processing engine 140 may obtain user instructions from the terminal(s) 130 via the network 120. The network 120 may include a public network (e.g., the Internet), a private network (e.g., a local area network (LAN), a wide area network (WAN))), a wired network (e.g., an Ethernet network), a wireless network (e.g., an 802.11 network, a Wi-Fi network), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the X-ray imaging system 100 may be connected to the network 120 to exchange data and/or information.

The terminal(s) 130 may include a mobile device 131, a tablet computer 132, a laptop computer 133, or the like, or any combination thereof. In some embodiments, the mobile device 131 may include a smart home device, a wearable device, a mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, footgear, eyeglasses, a helmet, a watch, clothing, a backpack, a smart accessory, or the like, or any combination thereof. In some embodiments, the mobile device may include a mobile phone, a personal digital assistant (PDA), a navigation device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a HoloLens™, a Gear VR™, etc. In some embodiments, the terminal(s) 130 may be part of the processing engine 140.

Figure 2:
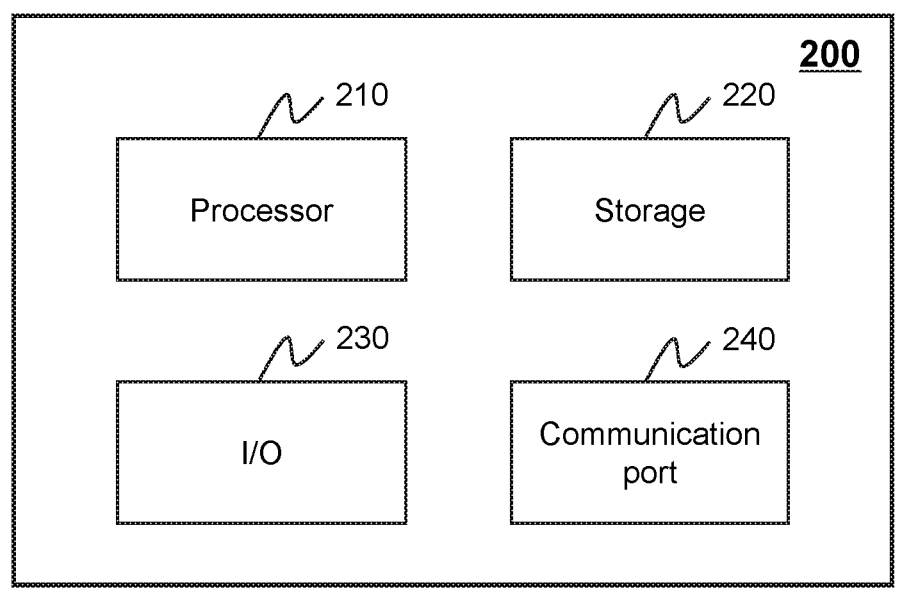
FIG. 2 is a schematic diagram illustrating exemplary hardware and/or software components of an exemplary computing device on which a processing engine may be implemented according to some embodiments of the present disclosure.

The processing engine 140 may process data and/or information obtained from the X-ray imaging device 110, the terminal(s) 130, and/or the storage device 150. For example, the processing engine 140 may process image data and reconstruct an image based on the image data. In some embodiments, the processing engine 140 may be a single server or a server group. The server group may be centralized or distributed. In some embodiments, the processing engine 140 may be local or remote. For example, the processing engine 140 may access information and/or data stored in the X-ray imaging device 110, the terminal(s) 130, and/or the storage device 150 via the network 120. As another example, the processing engine 140 may be directly connected to the X-ray imaging device 110, the terminal(s) 130, and/or the storage device 150 to access stored information and/or data. In some embodiments, the processing engine 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing engine 140 may be implemented by a computing device 200 having one or more components as illustrated in FIG. 2. In some embodiments, the processing engine 140, or a portion of the processing engine 140 may be integrated into the X-ray imaging device 110.

The storage device 150 may store data, instructions, and/or any other information. In some embodiments, the storage device 150 may store data obtained from the terminal(s) 130 and/or the processing engine 140. In some embodiments, the storage device 150 may store data and/or instructions that the processing engine 140 may execute or use to perform exemplary methods described in the present disclosure. In some embodiments, the storage device 150 may include a mass storage, removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random-access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more other components of the X-ray imaging system 100 (e.g., the processing engine 140, the terminal(s) 130). One or more components of the X-ray imaging system 100 may access the data or instructions stored in the storage device 150 via the network 120. In some embodiments, the storage device 150 may be directly connected to or communicate with one or more other components of the X-ray imaging system 100 (e.g., the processing engine 140, the terminal(s) 130). In some embodiments, the storage device 150 may be part of the processing engine 140.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the processing engine 140 and the X-ray imaging device 110 may be integrated into one single device. However, those variations and modifications do not depart the scope of the present disclosure.

FIG. 2 is a schematic diagram illustrating exemplary hardware and/or software components of an exemplary computing device 200 on which the processing engine 140 may be implemented according to some embodiments of the present disclosure. As illustrated in FIG. 2, the computing device 200 may include a processor 210, a storage 220, an input/output (I/O) 230, and a communication port 240.

The processor 210 may execute computer instructions (e.g., program code) and perform functions of the processing engine 140 in accordance with techniques described herein. The computer instructions may include, for example, routines, programs, objects, components, data structures, procedures, modules, and functions, which perform particular functions described herein. For example, the processor 210 may process image data obtained from the X-ray imaging device 110, the terminal(s) 130, the storage device 150, and/or any other component of the X-ray imaging system 100. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combination thereof.

Merely for illustration, only one processor is described in the computing device 200. However, it should be noted that the computing device 200 in the present disclosure may also include multiple processors. Thus operations and/or method steps that are performed by one processor as described in the present disclosure may also be jointly or separately performed by the multiple processors. For example, if in the present disclosure the processor of the computing device 200 executes both process A and process B, it should be understood that process A and process B may also be performed by two or more different processors jointly or separately in the computing device 200 (e.g., a first processor executes process A and a second processor executes process B, or the first and second processors jointly execute processes A and B).

The storage 220 may store data/information obtained from the X-ray imaging device 110, the terminal(s) 130, the storage device 150, and/or any other component of the X-ray imaging system 100. The storage 220 may be similar to the storage device 150 described in connection with FIG. 1, and the detailed descriptions are not repeated here.

The I/O 230 may input and/or output signals, data, information, etc. In some embodiments, the I/O 230 may enable a user interaction with the processing engine 140. In some embodiments, the I/O 230 may include an input device and an output device. Examples of the input device may include a keyboard, a mouse, a touchscreen, a microphone, a sound recording device, or the like, or a combination thereof. Examples of the output device may include a display device, a loudspeaker, a printer, a projector, or the like, or a combination thereof. Examples of the display device may include a liquid crystal display (LCD), a light-emitting diode (LED)-based display, a flat panel display, a curved screen, a television device, a cathode ray tube (CRT), a touchscreen, or the like, or a combination thereof.

The communication port 240 may be connected to a network (e.g., the network 120) to facilitate data communications. The communication port 240 may establish connections between the processing engine 140 and the X-ray imaging device 110, the terminal(s) 130, and/or the storage device 150. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee link, a mobile network link (e.g., 3G, 4G, 5G), or the like, or any combination thereof. In some embodiments, the communication port 240 may be and/or include a standardized communication port, such as RS232, RS485. In some embodiments, the communication port 240 may be a specially designed communication port. For example, the communication port 240 may be designed in accordance with the digital imaging and communications in medicine (DICOM) protocol.

Figure 3:
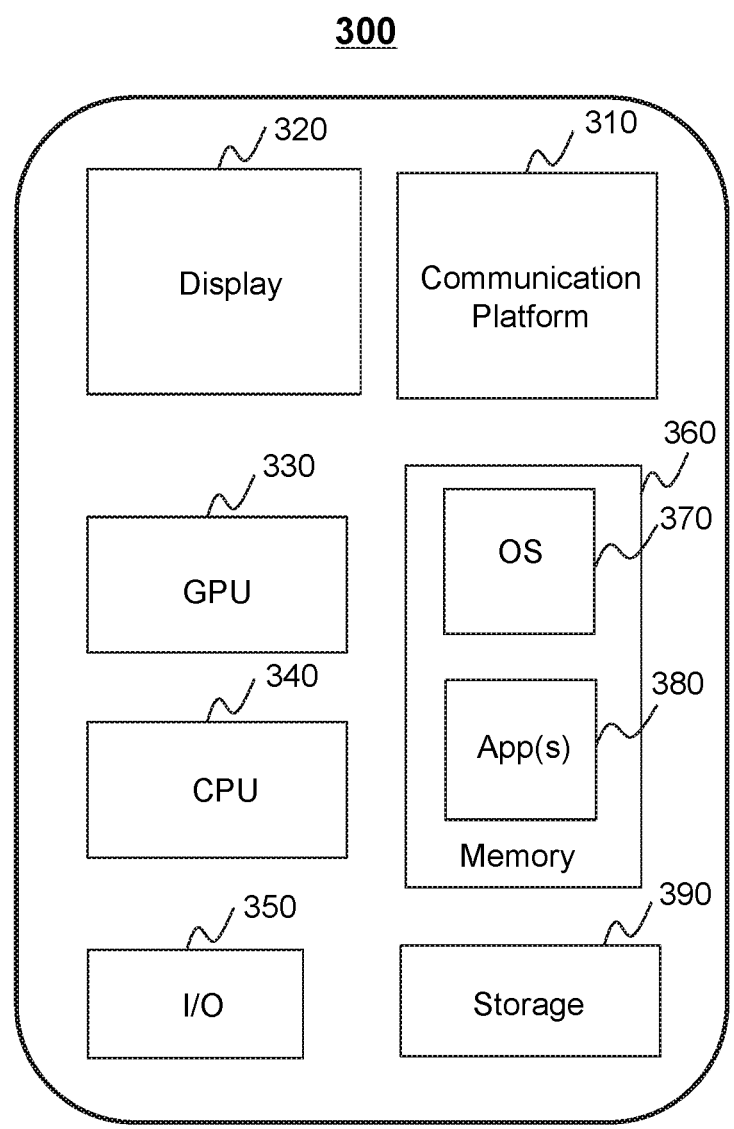
FIG. 3 is a schematic diagram illustrating exemplary hardware and/or software components of an exemplary mobile device on which a terminal may be implemented according to some embodiments of the present disclosure.

FIG. 3 is a schematic diagram illustrating exemplary hardware and/or software components of an exemplary mobile device 300 on which the terminal(s) 130 may be implemented according to some embodiments of the present disclosure. As illustrated in FIG. 3, the mobile device 300 may include a communication platform 310, a display 320, a graphics processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS™, Android™, Windows Phone™) and one or more applications 380 may be loaded into the memory 360 from the storage 390 in order to be executed by the CPU 340. The applications 380 may include a browser or any other suitable mobile apps for receiving and rendering information respect to image processing or other information from the processing engine 140. User interactions with the information stream may be achieved via the I/O 350 and provided to the processing engine 140 and/or other components of the X-ray imaging system 100 via the network 120.

To implement various modules, units, and their functionalities described in the present disclosure, computer hardware platforms may be used as the hardware platform(s) for one or more of the elements described herein. A computer with user interface elements may be used to implement a personal computer (PC) or any other type of workstation or external device. A computer may also act as a server if appropriately programmed.

Figure 4:
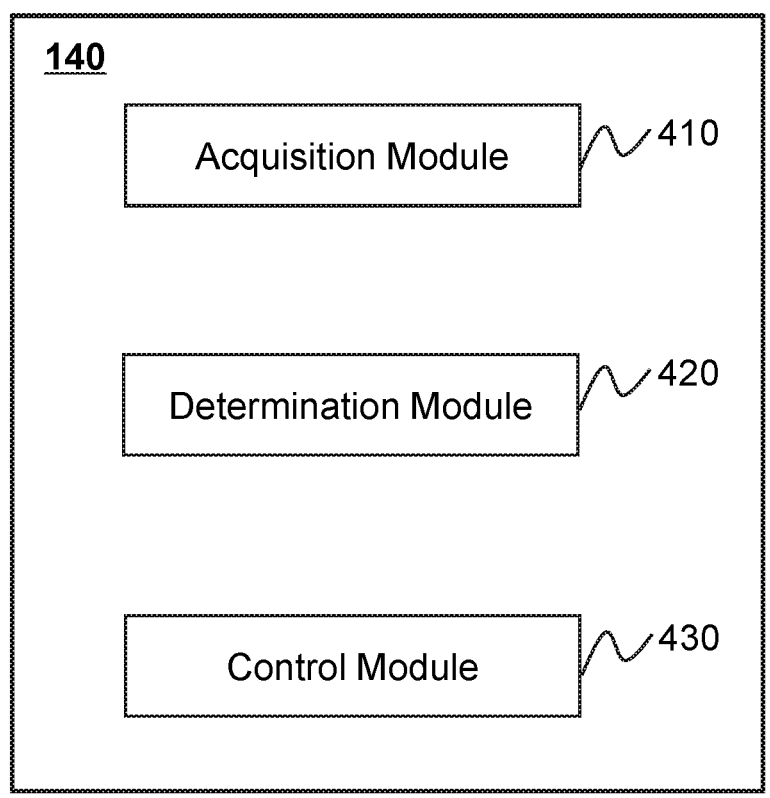
FIG. 4 is a block diagram illustrating an exemplary processing engine according to some embodiments of the present disclosure.

FIG. 4 is a schematic diagram illustrating an exemplary processing engine 140 according to some embodiments of the present disclosure. The processing engine 140 may include an acquisition module 410, a determination module 420, and a control module 430. At least a portion of the processing engine 140 may be implemented on a computing device 200 as illustrated in FIG. 2 or a mobile device 300 as illustrated in FIG. 3.

The acquisition module 410 may be configured to acquire information or instructions related to the X-ray imaging system 100. For example, the acquisition module 410 may acquire a speed of a suspension device 116 at a point (i.e., a reference point) on a rail 115 during its movement along the rail 115. The speed of the suspension device 116 may be acquired from one or more components of the X-ray imaging system 100, such as a speed sensor mounted on the rail 115, a position encoder, and/or the determination module 420. As another example, the acquisition module 410 may obtain a request from a user to control the suspension device 116 via, such as the terminal 130 or a control panel mounted on the suspension device 116.

The determination module 420 may be configured to determine information related to the X-ray imaging system 100. For example, the determination module 420 may determine the speed of the suspension device 116 at a point on the rail 115 based on the distance between the suspension device 116 and the detector 112 and a period. Merely by way of example, the speed of the suspension device 116 at a point on the rail 115 may be determined based on the change of the distance between the suspension device 116 and the detector 112 over a period during which the suspension device 116 passes through the point. The determination module 420 may also transmit the determined speed to the acquisition module 410. As another example, the determination module 420 may determine whether a speed of the suspension device 116 at a reference point on the rail 115 is less than a threshold speed. The threshold speed may be a default parameter stored in a storage device (e.g., the storage device 150, the storage 390). Additionally or alternatively, the threshold speed may be set manually or be determined by one or more components of the X-ray imaging system 100 according to different situations.

The control module 430 may be configured to actuate a control device to control the operating state of the suspension device 116. The control device may control the operating state of the suspension device 116 and include any combination of mechanisms to implement the functions thereof. The suspension device 116 may have a plurality of operating states, for example, a locked state, a manual movement state, an automatic movement state, a shutdown state, and/or a sleep state. In some embodiments, the control module 430 may actuate the control device by sending an instruction to the control device via, for example, the network 120. Details regarding the control device and/or the operating state of the suspension device 116 may be found elsewhere in the present disclosure (e.g., FIG. 6 and the relevant descriptions thereof).

It should be noted that the above description regarding the processing engine 140 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, the processing engine 140 may include a storage module configured to store data generated by the above-mentioned modules of the processing engine 140. For example, one or more modules may be integrated into a single module to perform the functions thereof. Merely by way of example, the acquisition module 410 and the determination module 420 may be integrated into a module to acquire and analyze information.

Figure 5:
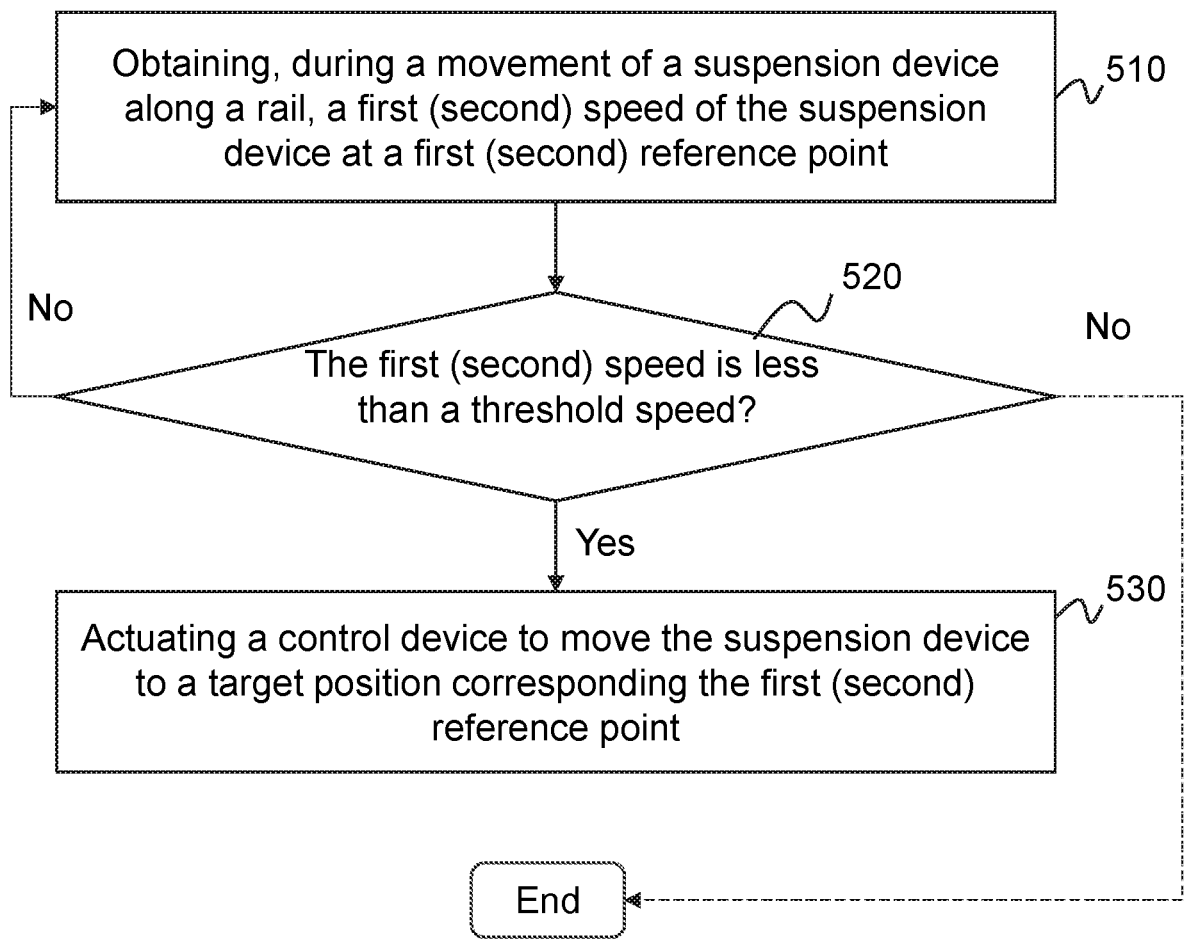
FIG. 5 is a flowchart illustrating an exemplary process for controlling a suspension device according to some embodiments of the present disclosure.

FIG. 5 is a flowchart illustrating an exemplary process for controlling a suspension device according to some embodiments of the present disclosure. In some embodiments, one or more operations of the process 500 illustrated in FIG. 5 may be implemented in the X-ray imaging system 100 illustrated in FIG. 1. For example, the process 500 illustrated in FIG. 5 may be stored in the storage device 150 in the form of instructions, and invoked and/or executed by the processing engine 140 (e.g., the processor 210 of the computing device 200 as illustrated in FIG. 2, the CPU 340 of the mobile device 300 as illustrated in FIG. 3).

In some embodiments, the suspension device to be controlled may be a suspension device 116 of an X-ray imaging device 110 as described in connection with FIG. 1. The suspension device 116 may include an X-ray source 113 and be suspended from a rail 115. The suspension device 116 may be movable and configured to move along the rail 115, and the X-ray source 113 may move with the suspension device 116. To scan different objects or different portions of an object, the X-ray source 113 may need to be configured at different positions with respect to the detector 112. For example, to scan different portions of a patient, the distance between the X-ray source 113 and the detector 112 may be different. As used herein, the distance between the X-ray source 113 and the detector 112 may be referred to as a source to image-receptor distance (SID) of the X-ray imaging device 110.

The rail 115 may include one or more target positions for the suspension device 116. The suspension device 116 may be moved to one of the target positions manually by a user or automatically by a control device. In some embodiments, the target position(s) may be associated with the SID(s) of the X-ray imaging device 110. When the suspension device 116 is moved to one of the target positions, the SID of the X-ray imaging device 110 may change to a desired value, and the X-ray source 113 may emit X-rays toward an object at a desired position. For example, the suspension device 116 may be moved to a target position at which the SID of the X-ray imaging device 110 may be 1.5 meters. In some embodiments, the number of target positions along the rail 115 may be any suitable number. The target position(s) may be any suitable position on the rail 115. In some embodiments, the target position(s) of the suspension device 116 may be default settings stored in a storage device (e.g., the storage device 150, the storage 390). Additionally or alternatively, the target position(s) may be set manually by a user or be determined by one or more components of the X-ray imaging system 100 (e.g., the processing engine 140) according to different situations.

In some embodiments, the rail 115 may include one or more reference points corresponding to a target position. A reference point corresponding to the target position may be configured at a position close to the target position. For example, a reference point may be configured at any position within a predetermined distance from the target position. The predetermined distance may be in a range of 10 to 110 mm. For example, the predetermined distance may be 90 mm, 100 mm, or 110 mm. In some embodiments, the predetermined distance may be restricted in a subrange of 10 to 30 mm, 30 to 50 mm, 50 to 90 mm, or 90 to 110 mm. The predetermined distance may be a default parameter stored in a storage device (e.g., the storage device 150, the storage 390). Additionally or alternatively, the predetermined distance may be determined or adjusted according to different situations by a user or one or more components of the X-ray imaging system 100 (e.g., the processing engine 140).

In some embodiments, the reference point(s) of the suspension device 116 may be default settings stored in a storage device (e.g., the storage device 150, the storage 390). Additionally or alternatively, the reference point(s) may be set manually by a user or be determined by one or more components of the X-ray imaging system 100 (e.g., the processing engine 140) according to different situations. In some embodiments, a reference point corresponding to a target position may be determined based on the predetermined distance by, such as the determination module 420. For example, the determination module 420 may designate one or more points on the rail located within the predetermined distance from the target position as the reference point(s) corresponding to the target position. Additionally or alternatively, the determination module 420 may designate one or more points between the target position and the current position of the suspension device 116, and located within the predetermined distance from the target position as the reference point(s) corresponding to the target position.

The reference point(s) corresponding to the target position may serve as a basis for determining whether the suspension device 116 is configured to be moved to the target position. For example, a user may move the suspension device 116 (or a portion thereof) to move the suspension device 116 along the rail 115 to a desired position. If the user wishes to move the suspension device 116 to the target position, he or she is supposed to slow down the speed of moving when the suspension device 116 is about to get to the target position. Accordingly, if the speed of the suspension device 116 at a reference point close to the target position is less than a threshold speed, the suspension device 116 is supposed to be moved to the target position by the user.

In some embodiments, the rail 115 may include a plurality of reference points corresponding to a target position. The plurality of reference points may be located at the same side of the target position along the rail 115. Additionally or alternatively, the reference points may be located on different sides of the target position along the rail 115. In some embodiments, different target positions may correspond to the same or different number of reference points. More descriptions regarding the arrangement of the target position(s) and the reference point(s) along the rail 115 may be found elsewhere in the present disclosure (e.g., FIGS. 7 to 9 and the relevant descriptions thereof).

For illustration purposes, the control of the suspension device 116 based on a first reference point is described in the present disclosure as an example. It should be noted that the descriptions below are merely provided for illustration purposes, and not intended to limit the scope of the present disclosure.

In 510, the acquisition module 410 may obtain a first speed of the suspension device 116 at the first reference point during a movement of the suspension device 116 along the rail 115. The first reference point may correspond to a first target position at the rail 115. The first reference point may be any position close to the first target position. For example, the first reference point may be located within a predetermined distance from the first target position. In some embodiments, the rail 115 may include one or more target positions and one or more reference points corresponding to the target position(s). The first reference point may be the reference point most recently passed through by the suspension device 116 during its movement.

In some embodiments, the acquisition module 410 may obtain the first speed of the suspension device 116 at the first reference point from one or more components of the X-ray imaging system 100. For example, a speed sensor may be mounted at the first reference point on the rail 115. The speed sensor may detect the first speed and transmit the first speed to the acquisition module 410. As another example, the X-ray imaging system 100 may include a position encoder configured to encode the position the of the suspension device 116 along the rail 115. For example, the position encoder may detect the distance between the suspension device 116 and the detector 112. The first speed may be determined based on the distance between the suspension device 116 and the detector 112 and a period. Merely by way of example, the first speed may be determined based on the change of the distance between the suspension device 116 and the detector 112 over a period during which the suspension device 116 passes through the first reference point. The first speed may be determined by, such as the position encoder and/or the determination module 420, and further be transmitted to the acquisition module 410.

In some embodiments, the speed sensor or the determination module 420 may detect the first speed of the suspension device 116 at the first reference point continuously or periodically. When the speed sensor or the determination module 420 detects that the first speed is greater than 0, the speed sensor or the determination module 420 may transmit the first speed to the acquisition module 410. Alternatively, the speed sensor or the determination module 420 may detect the first speed at the moment or a time substantially close to the moment when the suspension device 116 passes through the first reference point, and transmit the first speed to the acquisition module 410.

In 520, the determination module 420 may determine whether the first speed of the suspension device 116 at the first reference point is less than a threshold speed. The threshold speed may be a default parameter stored in a storage device (e.g., the storage device 150, the storage 390). Additionally or alternatively, the threshold speed may be set manually or be determined by one or more components of the X-ray imaging system 100 according to different situations. The threshold speed may be any positive value. For example, the threshold speed may be 1 mm/s, 10 mm/s, 20 mm/s, 50 mm/s, 100 mm/s, or any suitable value. In some embodiments, the threshold speed may be in a range of 1 to 100 mm/s. In some embodiments, the threshold speed may be restricted in a subrange of 1 to 10 mm/s, 10 to 20 mm/s, 20 to 40 mm/s, or 50 to 100 mm/s.

In response to the determination that the first speed of the suspension device 116 at the first reference point is less than the threshold speed, the process 500 may proceed to 530. In 530, the control module 430 may actuate a control device to move the suspension device 116 to the target position corresponding to the first reference point (i.e., the first target position). Under the control of the control device, the suspension device 116 may be automatically moved to the first target position. In some embodiments, the suspension device 116 may be moved to the first target position by the control device at a constant speed. In some embodiments, the control device may include a clutch and a motor. The control device may control the state of the suspension device 116 via the clutch and the motor. More descriptions regarding the control of the suspension device 116 by the control device may be found elsewhere in the present disclosure (e.g., FIG. 6 and the relevant descriptions thereof).

On the other hand, upon the determination that the first speed is not less than the threshold speed, the process 500 may be terminated, and the suspension device 116 may be maintained in its current state (e.g., being manually moved by the user).

In some embodiments, the rail 115 may further include a second reference point. The suspension device 116 may pass through the second reference point after passing through the first reference point. The second reference point may correspond to the same or a different target position as the first reference point. For example, the second reference point may also correspond to the first target position. The first and second reference points may locate at the same side of the first target position. Alternatively, the second reference point may correspond to a second target position. Upon the determination that the first speed is not less than the threshold speed, the process 500 may proceed to 510 to further obtain a second speed of the suspension device 116 at the second reference point during the movement of the suspension device 116 along the rail 115. In 520, the determination module 420 may determine whether the second speed is less than the threshold speed. In response to the determination that the second speed is less than the threshold speed, the process 500 may proceed to 530. The control module 430 may actuate the control device to move the suspension device 116 to the target position corresponding to the second reference point. On the other hand, upon the determination that the second speed is not less than the threshold speed, the process 500 may be terminated. Alternatively, the process 500 may proceed to 510 to obtain a speed of the suspension device 116 at a reference point other than the first or second reference point.

In some embodiments, the iteration of 510 to 520 may be repeated until the speed of the suspension device 116 at a certain reference point is less than the threshold speed or the suspension device 116 passes through all the reference points along the rail 115. If the speed of the suspension device 116 at a reference point is less than the threshold speed, the process 500 may proceed to 530, and the control module 430 may actuate the control device to move the suspension device 116 to the target position corresponding to the reference point in 530. If the suspension device 116 passes through all the reference points, the process 500 may be terminated.

It should be noted that the above description of the process 500 is merely provided for the purpose of illustration, and not intended to limit the scope of the present disclosure. For persons having ordinary skills in the art, multiple variations and modifications may be made to the process 500 under the teachings of the present disclosure. However, those variations and modifications do not depart from the scope of the present disclosure. In some embodiments, one or more steps may be added or omitted. For example, the suspension device 116 may have one or more operating states and change its operating state during the implementation of the process 500. More descriptions regarding the operating state of the suspension device 116 may be found elsewhere in the present disclosure (e.g., FIG. 6 and the relevant descriptions thereof).

Figure 6:
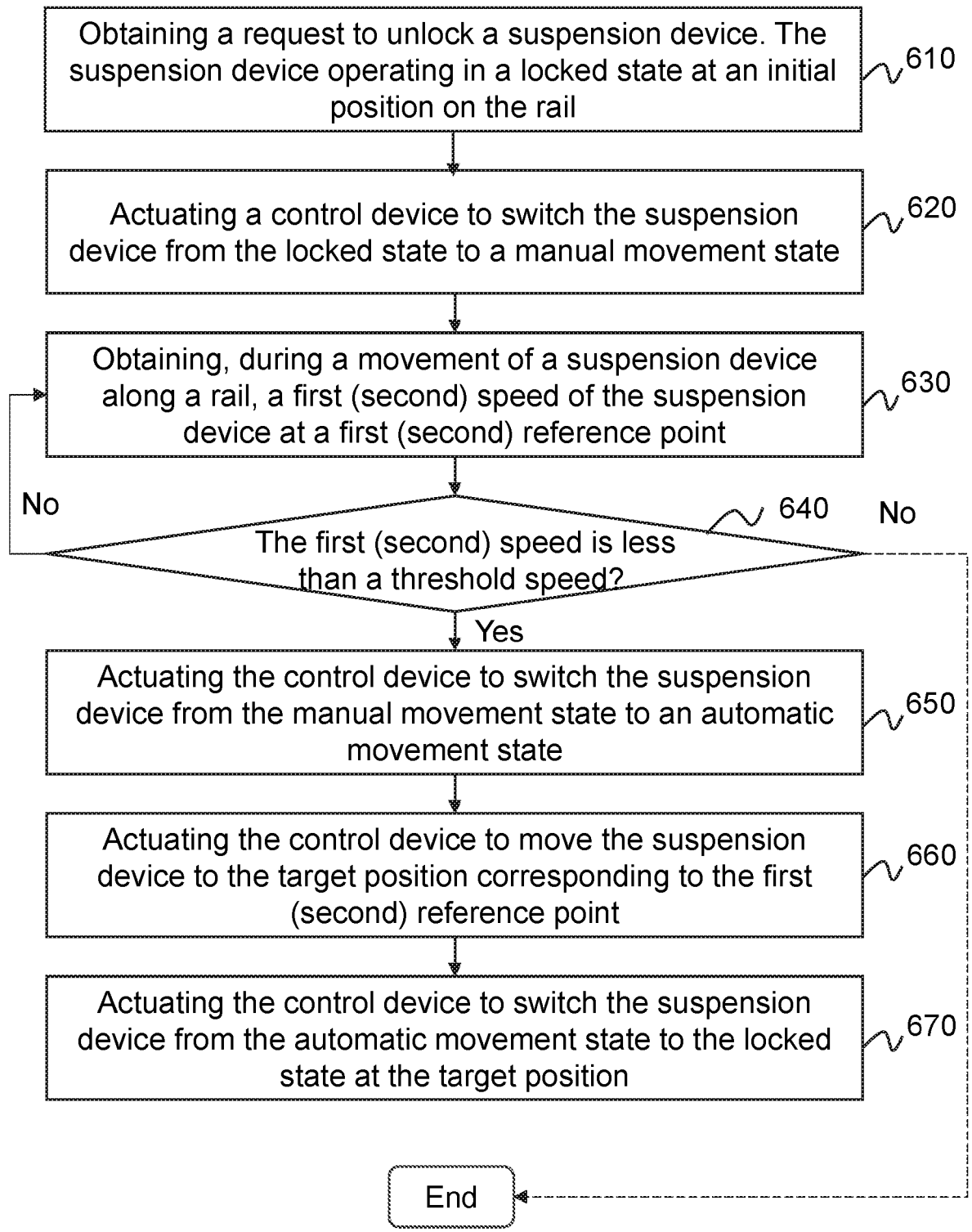
FIG. 6 is a flowchart illustrating an exemplary process for controlling a suspension device according to some embodiments of the present disclosure.

FIG. 6 is a flowchart illustrating an exemplary process for controlling a suspension device according to some embodiments of the present disclosure. In some embodiments, one or more operations of the process 600 illustrated in FIG. 6 for controlling a suspension device may be implemented in the X-ray imaging system 100 illustrated in FIG. 1. For example, the process 600 illustrated in FIG. 6 may be stored in the storage device 150 in the form of instructions, and invoked and/or executed by the processing engine 140 (e.g., the processor 210 of the computing device 200 as illustrated in FIG. 2, the CPU 340 of the mobile device 300 as illustrated in FIG. 3).

In some embodiments, the suspension device 116 may have a plurality of operating states, and the process 600 is an embodiment of the process 500. The operating state of the suspension device 116 may change during its movement along the rail 115. Exemplary operating states of the suspension device 116 may include but are not limited to a locked state, a manual movement state, an automatic movement state, or the like, or any combination thereof. In the locked state, the suspension device 116 may be locked onto the rail 115 and immovable. In the manual movement state, the suspension device 116 can be moved by a user along the rail 115. In the automatic movement state, the suspension device 116 may be automatically moved along the rail 115 by, for example, a motor (i.e., a component of the control device).

In some embodiments, the operating state of the suspension device 116 may be controlled by the control device. The control device may include a clutch and a motor. The suspension device 116 may operate in the locked state when the clutch is closed and the motor is turned off. The suspension device 116 may operate in the manual movement state when the clutch is open and the motor is turned off. The suspension device 116 may operate in the automatic movement state when the clutch is closed and the motor is turned on. It should be noted that the above descriptions of the control device are merely provided for the purposes of illustration, and not intended to limit the scope of the present disclosure. The control device may include any combination of mechanisms to implement the functions thereof. Merely by way of example, the control device may include a brake and a motor. The suspension device 116 may operate in the locked state when the brake is activated and the motor is turned off. The suspension device 116 may operate in the manual movement state when the brake is deactivated and the motor is turned off. The suspension device 116 may operate in the automatic movement state when the brake is deactivated and the motor is turned on. For illustration purpose, the present disclosure takes a control device including a clutch and a motor as an example.

In 610, the acquisition module 410 may obtain a request to unlock the suspension device 116. The suspension device 116 may operate in the locked state at its initial position on the rail 115. The initial position on the rail 115 may be any position of the rail 115. For example, the initial position may be one of the two end points of the rail 115. In some embodiments, the clutch may be closed, and the motor may be turned off when the suspension device 116 is at its initial position to prevent the suspension device 116 from moving.

In some embodiments, the acquisition module 410 may obtain the request from a user via one or more components of the X-ray imaging system 100, such as the terminal 130 or a control panel mounted on the suspension device 116. Merely by way of example, the interface of the control panel mounted on the suspension device 116 may include one or more interface elements (e.g., keys) configured to control the operating states of the suspension device 116. A user may initiate the request by, for example, clicking or pressing a key to unlock the suspension device 116. In some embodiments, the user may click a key to open the clutch so that the suspension device 116 may be unlocked. When the suspension device 116 is unlocked, the user may be able to move the suspension device 116 manually.

In 620, the control module 430 may actuate the control device to switch the suspension device 116 from the locked state to a manual movement state. For example, the control device may open the clutch to switch the suspension device 116 from the locked state to the manual movement state. The motor of the control device may be maintained in the off state.

In 630, the acquisition module 410 may obtain, during the movement of the suspension device 116 along the rail 115, a first speed of the suspension device 116 at a first reference point. In 640, the determination module 420 may determine whether the first speed of the suspension device 116 at the first reference point is less than a threshold speed. Steps 630 and 640 may be performed similarly with steps 510 and 520 respectively, and the detailed descriptions thereof are not repeated herein.

Upon the determination that the first speed of the suspension device at the first reference point is less than the threshold speed, the process 600 may proceed to 650. In 650, the control module 430 may actuate the control device to switch the suspension device 116 from the manual movement state to an automatic movement state. In some embodiments, the control device may close the clutch and turn on the motor to switch the suspension device 116 from the manual movement state to the automatic movement state.

In 660, the control module 430 may actuate the control device to move the suspension device to the target position corresponding to the first reference point. In some embodiments, the suspension device 116 may be moved by the motor of the control device from the first reference point to the target position corresponding to the first reference point.

In 670, the control module 430 may actuate the control device to switch the suspension device from the automatic movement state to the locked state at the target position. In some embodiments, when the suspension device 116 arrives at the target position, the control device may turn off the motor to switch the suspension device from the automatic movement state to the locked state. The clutch of the control device may be maintained in the closed state.

Referring back to 640, in response to the determination that the first speed of the suspension device at the first reference point is not less than the threshold speed, the process 600 may be terminated and the suspension device 116 may still operate in the manual movement state. In some embodiments, the rail 115 may include one or more other reference points. Steps 630 and 640 may be iteratively performed until the speed of the suspension device 116 at a certain reference point is less than the threshold speed or the suspension device 116 passes through all the reference points along the rail 115. If the speed of the suspension device 116 at a reference point is less than the threshold speed, the process 600 may proceed to 650. In 650, the control module 430 may actuate the control device to switch the suspension device 116 from the manual movement state to the automatic movement state. In 660, the control module 430 may actuate the control device to move the suspension device to the target position corresponding to the reference point. In 670, the control module 430 may actuate the control device to switch the suspension device from the automatic movement state to the locked state when the suspension device 116 arrives at the target position corresponding to the reference point. If the suspension device 116 passes through all the reference points, the process 600 may be terminated. The iteration of steps 630 and 640 may be similar to that of steps 510 and 520, and the detailed descriptions thereof are not repeated here.

It should be noted that the above description of the process 600 is merely provided for the purpose of illustration, and not intended to limit the scope of the present disclosure. For persons having ordinary skills in the art, multiple variations and modifications may be made to the process 600 under the teachings of the present disclosure. However, those variations and modifications do not depart from the scope of the present disclosure. In some embodiments, one or more steps may be added or omitted. For example, steps 610 and 620 may be merged into one step. As another example, steps 650 and 660 may be merged into one step. As yet another example, the suspension device 116 may operate at the manual movement state at the initial position, and the user may directly move the suspension device 116 along the rail 115. Steps 610 and 620 may be omitted.

Figure 7:
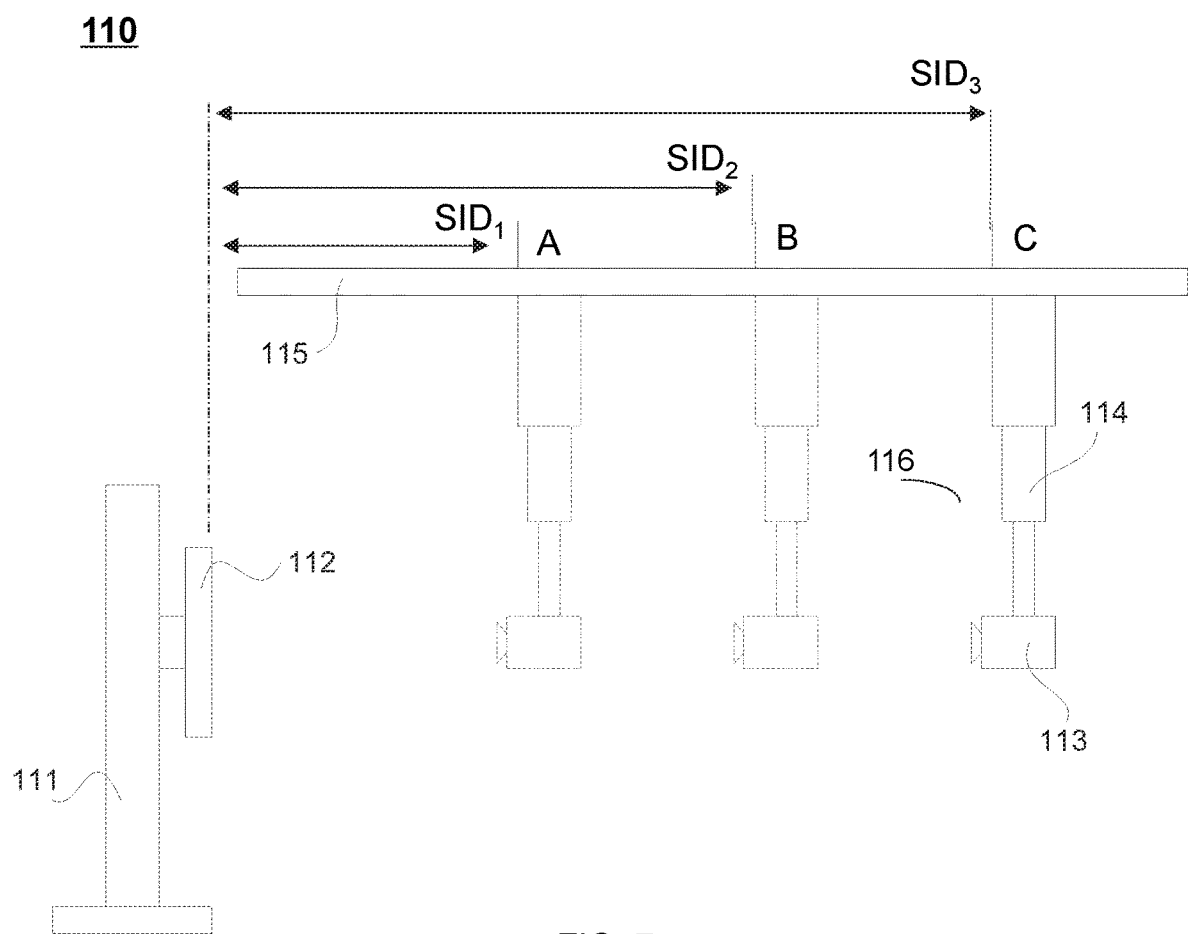
FIG. 7 is a schematic diagram illustrating exemplary source to image-receptor distance (SID) of an imaging device according to some embodiments of the present disclosure.

FIG. 7 is a schematic diagram illustrating exemplary SID of an X-ray imaging device 110 according to some embodiments of the present disclosure. As illustrated in FIG. 7, the X-ray imaging device 110 may include a support 111, a detector 112, a rail 115, and a suspension device 116.

The suspension device 116 may include an X-ray source 113 and be suspended from a rail 115. The suspension device 116 may be movable and configured to move along the rail 115. The X-ray source 113 may move with the suspension device 116, and the SID (i.e., the distance between the X-ray source 113 and the detector 112) of the X-ray imaging device 110 may change. As illustrated in FIG. 7, the suspension device 116 may be moved from position C to position B along the rail 115, and the SID of the X-ray imaging device 110 may change from $SID_3$ to $SID_2$. The suspension device 116 may be moved from position B to position A along the rail 115, and the SID of the X-ray imaging device 110 may change from $SID_2$ to $SID_1$. In some embodiments, the SID may be different when the X-ray imaging device 110 scans different objects or different portions of an object. The suspension device 116 may be moved to a desired position so that the SID of the X-ray imaging device 110 may change to a desired value.

Figure 8:
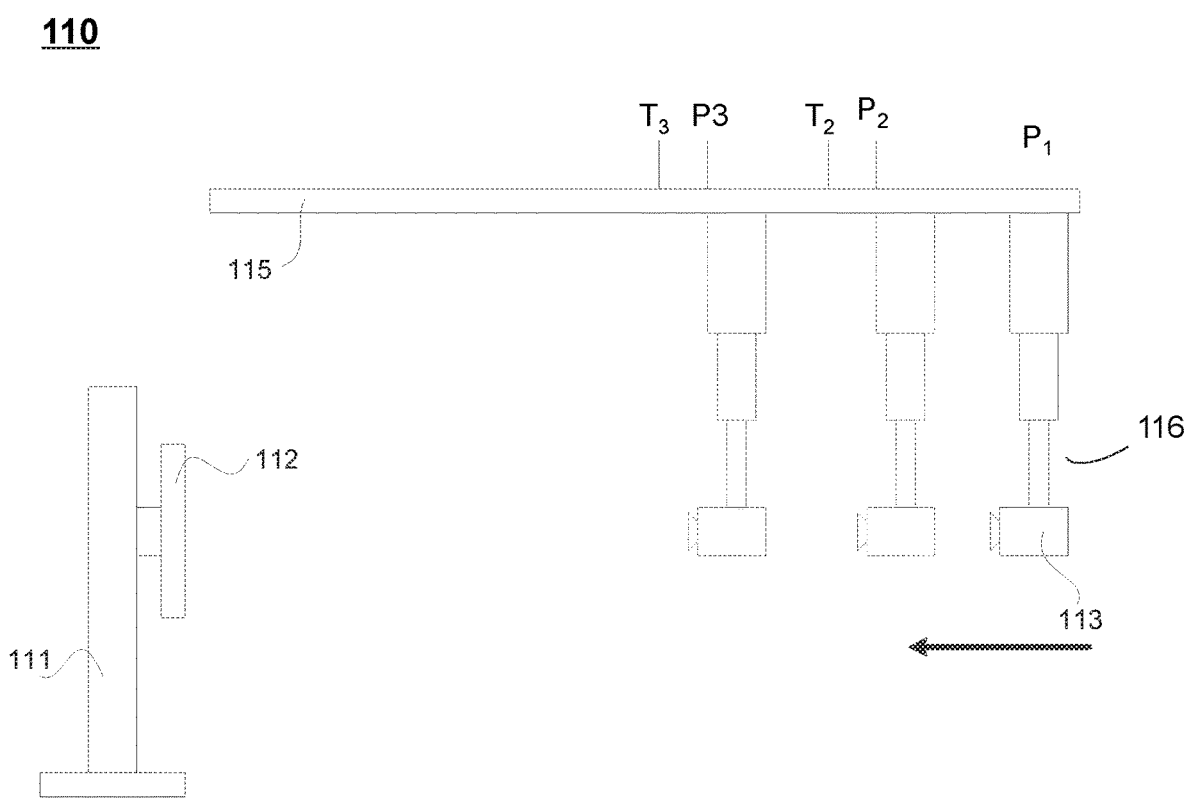
FIG. 8 is a schematic diagram illustrating an exemplary arrangement of target positions and reference points on a rail of an X-ray imaging device according to some embodiments of the present disclosure.

FIG. 8 is a schematic diagram illustrating an exemplary arrangement of target positions and reference points on a rail 115 of an X-ray imaging device 110 according to some embodiments of the present disclosure. As shown in FIG. 8, the rail 115 includes a target position $T_2$, a reference point $P_2$ corresponding to the target position $T_2$, a target position $T_3$, and a reference point $P_3$ corresponding to the target position $T_3$. The suspension device 116 locates at an initial position $P_1$ on the rail 115 and is moved by a user toward the detector 112 as indicated by the arrow in FIG. 8.

When the suspension device 116 passes through a reference point, the process 500 or 600 may be initiated or performed to control the movement of the suspension device 116. For example, the acquisition module 410 may obtain the speed of the suspension device 116 at the reference point $P_2$ at the moment or a time substantially close to the moment when the suspension device 116 passes through the reference point $P_2$. The determination module 420 may determine whether the speed of the suspension device 116 at the reference point $P_2$ is less a threshold speed. In response to the determination that the speed at the reference point $P_2$ is less than the threshold speed, the control module 430 may actuate a control device to move the suspension device 116 from the reference point $P_2$ to the corresponding target position $T_2$.

On the other hand, upon the determination that the speed at the reference point $P_2$ is not less than the threshold speed, the suspension device 116 may be maintained to be moved along the rail 115 by the user. For example, the suspension device 116 may be moved by the user and pass through the reference point $P_3$. Similarly, the speed of the suspension device 116 at the reference point $P_3$ may be acquired and analyzed. If the speed at the reference point $P_3$ is less than the threshold speed, the control module 430 may actuate the control device to move the suspension device 116 from the reference point $P_3$ to the corresponding target position $SID_3$.

Figure 9:
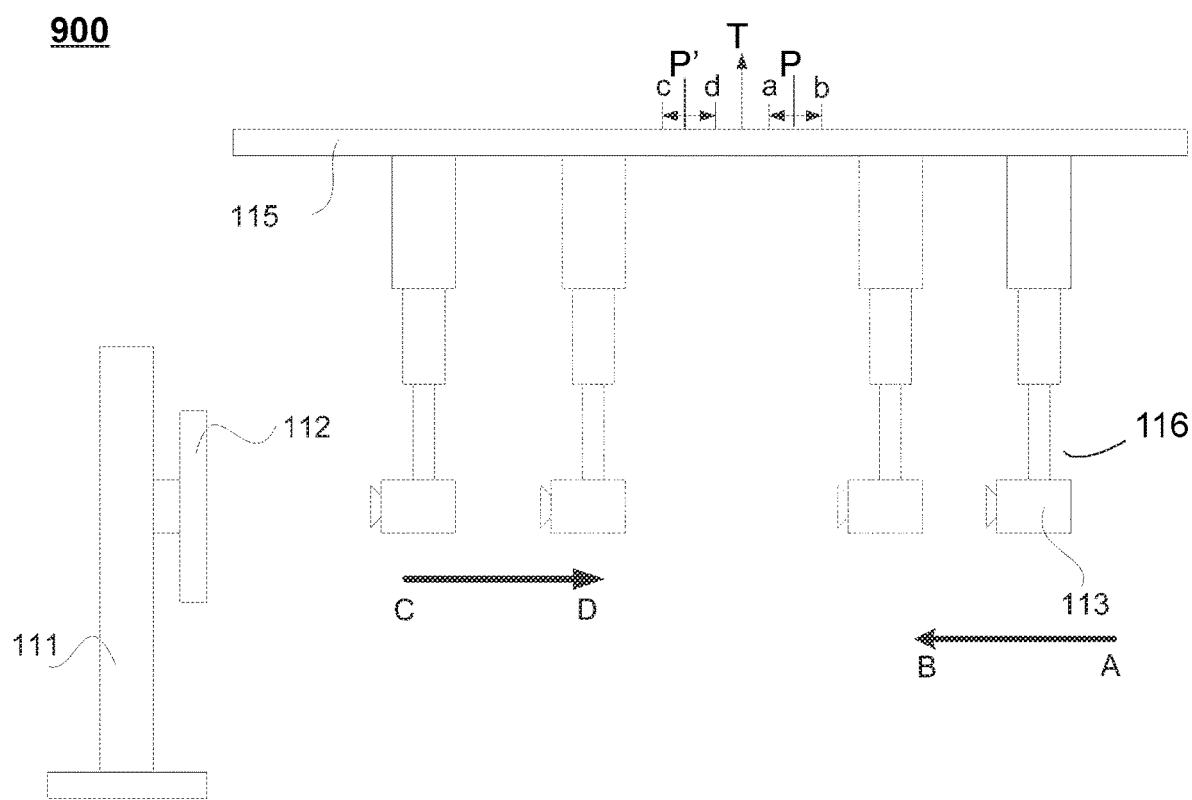
FIG. 9 is a schematic diagram illustrating an exemplary arrangement of a target position and reference points on a rail of an X-ray imaging device according to some embodiments of the present disclosure.

FIG. 9 is a schematic diagram illustrating an exemplary arrangement of a target position and reference points on a rail 115 of an X-ray imaging device 110 according to some embodiments of the present disclosure. In some embodiments, the rail 115 may include a plurality of reference points corresponding to a target position. At least one of the reference points may locate on one side of the target position, and at least one of the reference points may locate on another side of the target position along the rail 115. For example, as shown in FIG. 9, the rail 115 may include the target position T, and two reference points P and P' corresponding to the target position T. The reference point P and the reference point P' are located on different sides of the target position T.

In some embodiments, the reference point P may be any position located in the region [a, b] on the rail 115, and the reference point P' may be any position located in the region [c, d] on the rail 115. For illustration purposes, the distance between the target position T and the detector 112 may be 1.5 meters. The distance between the reference point P' and the detector 112 may be in the range of [1.4 m, 1.45 m], and the distance between the reference point P and the detector 112 may be in the range of [1.55 m, 1.6 m].

In some embodiments, the reference point may be determined based on the direction of the movement of the suspension device 116. For example, when suspension device 116 is moved toward the detector 112 (as indicated by arrow AB), the determination module 420 may determine the reference point P as the reference point corresponding to the target position T. When the suspension device 116 is moved far away from the detector 112 (as indicated by arrow CD), the determination module 420 may determine the reference point P' as the reference point corresponding to the target position T.

It should be noted that the examples illustrated in FIGS. 8 and 9 are merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the rail 115 may include any number of reference points and target positions. The reference point(s) and the target position(s) may be arranged at any position on the rail 115.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer-readable medium having computer readable program code embodied thereon.

A computer readable signal medium may include a propagated data signal with computer readable program code embodied therein, for example, in baseband or as part of a carrier wave. Such a propagated signal may take any of a variety of forms, including electromagnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object-oriented programming language such as Java, Scala, Smalltalk, Eiffel, JADE, Emerald, C++, C#, VB. NET, Python or the like, conventional procedural programming languages, such as the "C" programming language, Visual Basic, Fortran 2103, Perl, COBOL 2102, PHP, ABAP, dynamic programming languages such as Python, Ruby, and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software-only solution, for example, an installation on an existing server or mobile device.

Similarly, it should be appreciated that in the foregoing description of embodiments of the present disclosure, various features are sometimes grouped together in a single embodiment, figure, or description thereof to streamline the disclosure aiding in the understanding of one or more of the various inventive embodiments. This method of disclosure, however, is not to be interpreted as reflecting an intention that the claimed object matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/ or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A system, comprising:
an X-ray imaging device including a suspension device, the suspension device including an X-ray source and being suspended from a rail, the suspension device being movable along the rail, the rail including a first target position and a first reference point, the first reference point corresponding to the first target position;
a control device configured to control the suspension device, the control device comprising a driving component and a braking component;
a non-transitory storage device storing a set of instructions for controlling the suspension device; and
at least one processor configured to communicate with the non-transitory storage device, wherein when executing the set of instructions, the at least one processor is configured to cause the system to:
obtain, during a movement of the suspension device along the rail, a first speed of the suspension device at the first reference point;
determine whether the first speed of the suspension device at the first reference point is less than a threshold speed; and
in response to a determination that the first speed of the suspension device at the first reference point is less than the threshold speed, actuate the control device to automatically drive the suspension device to the first target position, wherein the driving component of the control device is activated and the braking component is deactivated when the control device automatically drives the suspension device to the first target position.

2. The system of claim 1, wherein:
the suspension device has a locked state and a manual movement state, under the locked state the suspension device being configured to be locked onto the rail, under the manual movement state the suspension device being configured to be manually moved by a user,
the suspension device operates in the locked state at an initial position of the suspension device on the rail, and
the at least one processor is further configured to cause the system to:
obtain a request to unlock the suspension device; and
actuate the control device to switch the suspension device from the locked state to the manual movement state.

3. The system of claim 2, wherein:
the suspension device further has an automatic movement state, under the automatic movement state, the suspension device being configured to be moved by the control device; and
to actuate the control device to automatically drive the suspension device to the first target position, the at least one processor is further configured to cause the system to:
actuate the control device to switch the suspension device from the manual movement state to the automatic movement state.

4. The system of claim 3, the at least one processor is further configured to cause the system to:
actuate the control device to switch the suspension device from the automatic movement state to the locked state at the first target position.

5. The system of claim 3, wherein:
the braking component includes a clutch and the driving component includes a motor,
the suspension device operates in the locked state when the clutch is closed and the motor is turned off,
the suspension device operates in the manual movement state when the clutch is open and the motor is turned off, and
the suspension device operates in the automatic movement state when the clutch is closed and the motor is turned on.

6. The system of claim 2, wherein:
the rail further includes a second target position and a second reference point, the second reference point corresponding to the second target position, and
the at least one processor is configured to cause the system to:
in response to a determination that the first speed of the suspension device at the first reference point is not less than the threshold speed, maintain the suspension device in the manual movement state;
obtain, during a movement of the suspension device along the rail, a second speed of the suspension device at the second reference point;
determine whether the second speed of the suspension device at the second reference point is less than the threshold speed; and
in response to the determination that the second speed of the suspension device at the second reference point is less than the threshold speed, actuate the control device to automatically drive the suspension device to the second target position.

7. The system of claim 1, wherein:
the rail includes a plurality of first reference points corresponding to the first target position, and
at least one of the plurality of first reference points locates on one side of the first target position and at least one of the plurality of first reference points locates on another side of the first target position along the rail.

8. The system of claim 1, wherein the at least one processor is further configured to cause the system to:
determine the first reference point corresponding to the first target position on the rail, a distance between the first reference point and the first target position being less than a predetermined distance.

9. The system of claim 1, wherein the braking component includes a brake.

10. The system of claim 1, wherein the first target position is associated with a source to image receptor distance (SID) of the X-ray imaging device.

11. A method implemented on a computing device having one or more processors and one or more non-transitory storage media, the method comprising:
obtaining, during a movement of a suspension device along a rail, a first speed of the suspension device at a first reference point on the rail, the suspension device including an X-ray source and being suspended from the rail, the suspension device being movable along the rail, the first reference point corresponding to a first target position on the rail, the suspension device being controlled by a control device, the control device including a driving component and a braking component;
determining whether the first speed of the suspension device at the first reference point is less than a threshold speed; and
in response to a determination that the first speed of the suspension device at the first reference point is less than the threshold speed, actuating the control device to automatically drive the suspension device to the first target position, wherein the driving component of the control device is activated and the braking component is deactivated when the control device automatically drives the suspension device to the first target position.

12. The method of claim 11, wherein:
the suspension device has a locked state and a manual movement state, under the locked state the suspension device being configured to be locked onto the rail, under the manual movement state the suspension device being configured to be manually moved by a user,
the suspension device operates in the locked state at an initial position of the suspension device on the rail, and the method further comprises:
obtaining a request to unlock the suspension device; and
actuating the control device to switch the suspension device from the locked state to the manual movement state.

13. The method of claim 12, wherein:
the suspension device further has an automatic movement state, under the automatic movement state, the suspension device being configured to be moved by the control device; and
the actuating the control device to automatically drive the suspension device to the first target position further comprises:
actuating the control device to switch the suspension device from the manual movement state to the automatic movement state.

14. The method of claim 13, further comprises:
actuating the control device to switch the suspension device from the automatic movement state to the locked state at the first target position.

15. The method of claim 13, wherein:
the braking component includes a clutch and the driving component includes a motor,
the suspension device operates in the locked state when the clutch is closed and the motor is turned off,
the suspension device operates in the manual movement state when the clutch is open and the motor is turned off, and
the suspension device operates in the automatic movement state when the clutch is closed and the motor is turned on.

16. The method of claim 12, wherein:
the rail further includes a second target position and a second reference point, the second reference point corresponding to the second target position, and the method further comprises:
 in response to a determination that the first speed of the suspension device at the first reference point is not less than the threshold speed, maintaining the suspension device in the manual movement state;
 obtaining, during a movement of the suspension device along the rail, a second speed of the suspension device at the second reference point;
 determining whether the second speed of the suspension device at the second reference point is less than the threshold speed; and
 in response to the determination that the second speed of the suspension device at the second reference point is less than the threshold speed, actuating the control device to automatically drive the suspension device to the second target position.

17. The method of claim 11, wherein:
the rail includes a plurality of first reference points corresponding to the first target position, and
at least one of the plurality of first reference points locates on one side of the first target position and at least one of the plurality of first reference points locates on another side of the first target position along the rail.

18. The method of claim 11, further comprises:
determining the first reference point corresponding to the first target position on the rail, a distance between the first reference point and the first target position being less than a predetermined distance.

19. The method of claim 11, wherein the braking component includes a brake.

20. A non-transitory computer-readable storage medium storing instructions that, when executed by at least one processor of a system, cause the system to perform a method, the method comprising:
 obtaining, during a movement of a suspension device along a rail, a first speed of the suspension device at a first reference point on the rail, the suspension device including an X-ray source and being suspended from the rail, the suspension device being movable along the rail, the first reference point corresponding to a first target position on the rail, the suspension device being controlled by a control device, the control device including a driving component and a braking component;
 determining whether the first speed of the suspension device at the first reference point is less than a threshold speed; and
 in response to a determination that the first speed of the suspension device at the first reference point is less than the threshold speed, actuating the control device to automatically drive the suspension device to the first target position, wherein the driving component of the control device is activated and the braking component is deactivated when the control device automatically drives the suspension device to the first target position.

\* \* \* \* \*